(12) United States Patent
Tanabe et al.

(10) Patent No.: US 11,666,615 B2
(45) Date of Patent: *Jun. 6, 2023

(54) METHOD FOR INDUCING PRODUCTION OF VASCULAR ENDOTHELIAL GROWTH FACTOR

(71) Applicants: Tadashi Tanabe, Osaka (JP); Keiichi Hukuda, Tokyo (JP); Takashi Kawakami, Tokyo (JP)

(72) Inventors: Tadashi Tanabe, Osaka (JP); Keiichi Hukuda, Tokyo (JP); Takashi Kawakami, Tokyo (JP)

(*) Notice: Subject to any disclaimer, the term of this patent is extended or adjusted under 35 U.S.C. 154(b) by 563 days.

This patent is subject to a terminal disclaimer.

(21) Appl. No.: 16/783,717

(22) Filed: Feb. 6, 2020

(65) Prior Publication Data
US 2020/0171109 A1 Jun. 4, 2020

Related U.S. Application Data

(63) Continuation of application No. 15/404,076, filed on Jan. 11, 2017, now abandoned, which is a continuation of application No. 13/393,062, filed as application No. PCT/JP2010/005321 on Aug. 30, 2010, now abandoned.

(30) Foreign Application Priority Data

Aug. 31, 2009 (JP) ................................. 2009-200900

(51) Int. Cl.
| | |
|---|---|
| A61K 35/76 | (2015.01) |
| A61K 31/5585 | (2006.01) |
| A61K 38/18 | (2006.01) |
| A61K 38/52 | (2006.01) |
| A61K 45/06 | (2006.01) |
| A61K 48/00 | (2006.01) |
| C12N 7/00 | (2006.01) |
| A61K 35/13 | (2015.01) |

(52) U.S. Cl.
CPC .......... *A61K 35/76* (2013.01); *A61K 31/5585* (2013.01); *A61K 38/1825* (2013.01); *A61K 38/1833* (2013.01); *A61K 38/1866* (2013.01); *A61K 38/52* (2013.01); *A61K 45/06* (2013.01); *A61K 48/005* (2013.01); *C12N 7/00* (2013.01); *C12Y 503/99004* (2013.01); *A61K 35/13* (2013.01); *C12N 2750/14132* (2013.01); *C12N 2750/14143* (2013.01); *C12N 2799/025* (2013.01)

(58) Field of Classification Search
None
See application file for complete search history.

(56) References Cited

U.S. PATENT DOCUMENTS

| 7,276,490 B1 | 10/2007 | Tanabe et al. |
| 2006/0099183 A1 | 5/2006 | Zoldhelyi et al. |

FOREIGN PATENT DOCUMENTS

| EP | 1 300 158 A1 | 4/2003 |
| EP | 1308517 A1 | 5/2003 |
| WO | WO-02/00258 A1 | 1/2002 |

OTHER PUBLICATIONS

Lau, et al. (2021) "Physiology, Prostaglandin I2", StatPearls Publishing, Treasure Island, FL, downloaded from https://www.ncbi.nlm.nih.gov/books/NBK562273/ on Feb. 27, 2021, 5 pages as printed. (Year: 2021).
Office Action issued in U.S. Appl. No. 16/373,388, dated Mar. 4, 2021.
Ito et al., "Adenoassociated Virus Mediated Prostacyclin Synthase Expression Prevents Pulmonary Arterial Hypertension in Rats", Hypertension, vol. 50, No. 3, pp. 531-536, XP055047327, ISSN: 0194-911X, DOI: 10.1161/YHYPERTENSIONAHA.107.091348, Sep. 1, 2007.
Koike et al., "Enhanced angiogenesis and improvement of neuropathy by cotransfection of human hepatocyte growth factor and prostacyclin synthase gene",The FASEB Journal, vol. 17, No. 6, pp. 779-781, XP055047311, ISSN: 0892-6638, DOI: 10.1096/fj.02-0754fje, Apr. 1, 2003.
Gelband et al., "Current perspectives on the use of gene therapy for hypertension", Circulation Research, Grune and Stratton, Baltimore, MD, US, vol. 87, No. 12, pp. 1118-1122, XP002219628, ISSN: 0009-7330, Dec. 8, 2000.
McKay et al., "Gene Transfer Therapy in Vascular Diseases", Cardiovascular Drug Reviews, Neva Press, Branford, CT, US, vol. 19, No. 3, pp. 245-262, XP0080503041, ISSN: 0897-5957, Jan. 1, 2001.
Barandon et al., "Gene Therapy for Chronic Peripheral Arterial Disease: What Role for the Vascular Surgeon?", Annals of Vascular Surgery, Quality Medical Publishing, St. Louis, MO, US, vol. 18, No. 6, pp. 758-765, XP005941311, ISSN: 0890-5096, DOI: 10.1007/S10016-004-0115-5, Nov. 1, 2004.
Takeshita et al, "Intramuscular Administration of Vascular Endothelial Growth Factor Induces Dose-Dependent Collateral Artery Augmentation in a Rabbit Model of Chronic Limb Ischemia," American Heart Association, Inc. Boston, MA, Circulation, vol. 90, No. 6, pp. 228-234, ISSN: 0009-7322, Nov. 1994.

(Continued)

*Primary Examiner* — Robert M Kelly
(74) *Attorney, Agent, or Firm* — Michael Best & Friedrich LLP

(57) ABSTRACT

The present invention relates to a method for inducing production of vascular endothelial growth factor (VEGF). The method includes administering, to an individual, a composition including adeno-associated virus (AAV) carrying a hPGIS gene coding for human prostacyclin synthase (hPGIS) which synthesizes prostaglandin $I_2$ ($PGI_2$).

4 Claims, 6 Drawing Sheets
(1 of 6 Drawing Sheet(s) Filed in Color)

(56) References Cited

OTHER PUBLICATIONS

Search Report issued in European Application No. 10811534.6-2107 / 2474325, dated Dec. 18, 2012.
Kawakami et al., "Gene Therapy Using AAV-PGIS Vector Improves a Necrosis of Limb Ischemia", Circulation Journal, vol. 74, No. SuDDlement 1, p. 623, Mar. 2010.
Kawakami et al., Adena-associated Virus mediated Prostaglandin I2 Synthase (PGIS) Gene Transfer Improves a Limb Ischemia, Circulation Journal, vol. 73, No. Supplement 1, pp. 592-593, Mar. 2009.
Hiraoka et al., "Enhanced Therapeutic Angiogenesis by Cotrasfection of Prostacyclin Synthase Gene or Optimization of Intramuscular Injection of Naked Plasmid DNA," Circulation, vol. 108, No. 21, pp. 2689-2696, Oct. 2003.
Kawakami et al., "AAV-PGIS gene transfer improves hypoxia-induced pulmonary hypertension in mice," Biochemical and Biophysical Research Communications, Elsevier Inc., vol. 363, No. 3, DD. 656-61, Sep. 2007.
Yan et al., "Superior neovascularization and muscle regeneration in ischemic skeletal muscles following VEGF gene transfer by rAAV1 pseudotyped vectors," Biochemical and Biophysical Research Communications, Elsevier Inc., vol. 336, No. 1, pp. 287-298, Oct. 2005.
Hauck et al., "Characterization of Tissue Tropism Determinants of Adena-Associated Virus Type 1," Journal of Virology. vol. 77, No. 4, pp. 2768-2774, Feb. 2003.
International Search Report issued in Application No. PCT/JP2010/005321, dated Oct. 19, 2010.
Nagaya, et al., "Gene Transfer of Human Prostacyclin Synthase Ameliorates Monocrotaline-Induced Pulmonary Hypertension in Rats" American Heart Association, Inc. May 24, 2000.
Sada et al., "Development of cardiovascular regenerative thereapy by activation of tissue stem cells," Comprehensive Study Report, Health Labor and Welfare Science Study, Regeneration Medicine Research Report, p. 5-10, Mar. 2008.
Nunaguchi, "Catheter-based prostacyclin synthase gene transfer prevents in-stent restenosis in rabbit atheromatous arteries," Cardiovascular Research, European Society of Cardiology, Elsevier B.V., vol. 61, No. 1, pp. 177-185, 2004.
Office Action issued in Japanese Application No. 2015-045546, dated Feb. 9, 2016.
Ito, et al. "Adenoassociated Virus-Mediated Prostacyclin Synthase Expression Prevents Pulmonary Arterial Hypertension in Rats", 50(3): 531-36, 2007.
Fu, et al. (2005) "Optimization of AAV Serotypes and Promoter for Increased Distribution of Expression in Both Somatic and Central Nervous System of Mice", Molecular Therapy, 11 (Supp 1 ): 8332.
Gupta, et al. (2003) "Cyclooxygenase-1 is Overexpressed and Promotes Angiogenic Growth Factor Production in Ovarian Cancer", Cancer Research, 63: 906-11). It is noted that several of the other proteins to be encoded also promote angiogenesis, e.g., E2F-1, ENOS.
Haidet (2008) "Long-term enhancement of skeletal muscle mass and strength by single gene administration of myostatin inhibitors", Proceedings of the National Academy of Science, USA., 105(11 ): 4318-22.

METHOD FOR INDUCING PRODUCTION OF VASCULAR ENDOTHELIAL GROWTH FACTOR

CROSS-REFERENCE TO RELATED APPLICATIONS

This application is a continuation of prior U.S. patent application Ser. No. 15/404,076, filed on Jan. 11, 2017, now abandoned, which is a continuation of U.S. patent application Ser. No. 13/393,062, filed on Feb. 28, 2012, now abandoned, which is a national stage filing under 35 U.S.C. 371 of International Patent Application No. PCT/JP2010/005321, filed Aug. 30, 2010, which claims priority to Japanese Patent Application No. 2009-200900, filed Aug. 31, 2009, the contents of each of which, including the specification, the claims, and the drawings, are incorporated herein by reference in their entirety.

BACKGROUND

The present invention relates to reinforcing materials for angiogenesis activities, which are useful pharmaceutical compositions for angiogenesis therapy. In particular, this invention relates to a method for inducing production of vascular endothelial growth factor (VEGF).

Western life-style and aging society of Japan yearly cause an marked increase in number of patients suffering from peripheral arterial disease (PAD), which is based on arteriosclerosis brought by risk factors such as aging, smoking, diabetes, hypertension and metabolic disorders of lipids. According to the report from American Heart Association, furthermore, popularization of noninvasive examination tests for PAD detected a contract rate of about 2-3% below age of 50 years and that of about 20% over 75 years old. And approximately about 40% PAD patients are known to show no indications.

Presently, there are, as therapeutic methods for PAD, treatments with drugs such as anti-platelets, vasodilator, and prostaglandins, or with vascular stent, and surgical bypass operation. However, effects by therapy with drugs are limited, and treatment with vascular stent or surgical bypass operation, the first choice of treatment for serious patients, are not always adopted. As PAD resistant to known therapeutic methods critical limb ischemia (CLI) is known. CLI is defined as the state accompanying chronic ischemic pain at rest and ischemic skin disorder (ulcer and gangrene). Prognosis of CLI is gloomy. At one year after the onset of CLI it is known that 25% of patients lose a leg(s) and 25% of patients are dead.

In recent clinical research various cell therapy and gene therapy as endovascular treatments of PAD. Bone marrow mononuclear cells and peripheral mononuclear cells are used for the cell therapy. Recombinant angiogenesis factors are used for the gene therapy. These factors used for the gene therapy, for example, are vascular endothelial growth factor (VEGF), fibroblast growth factor (FGF), and hepatic growth factor (HGF). These genes for angiogenesis factors enhances angiopoiesis in ischemic tissues by expressing these factors. And by the use of these factors it was possibly ascertained that development of collateral blood vessels in model animals of heart or limb ischemia is promoted and/or enhanced (Circulation 90, 11-228-11-234 (1994).

Therapy for vasculopathy with above-mentioned angiogenesis factors is designated as "angiogenesis therapy". More recently, using gene for above-mentioned angiogenesis factors therapeutic angiogenesis studies in ischemic and arterial diseases have been actively carried out.

Furthermore, a drug composition of angiogenesis therapy is one described in WO2002/000258. The drug composition of angiogenesis therapy mentioned in this document is the one containing gene for HGF or VEGF and prostacyclin synthase gene as effective components.

SUMMARY

The present invention is concerned with a method for inducing production of vascular endothelial growth factor (VEGF). The method includes administering, to an individual, a composition including adeno-associated virus (AAV) carrying a hPGIS gene coding for human prostacyclin synthase (hPGIS) which synthesizes prostaglandin $I_2$ ($PGI_2$).

The patent or application file contains at least one draw executed in color. Copies of this patent or patent application publication with color drawing(s) will be provided by the Office upon request and payment of the necessary fee.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
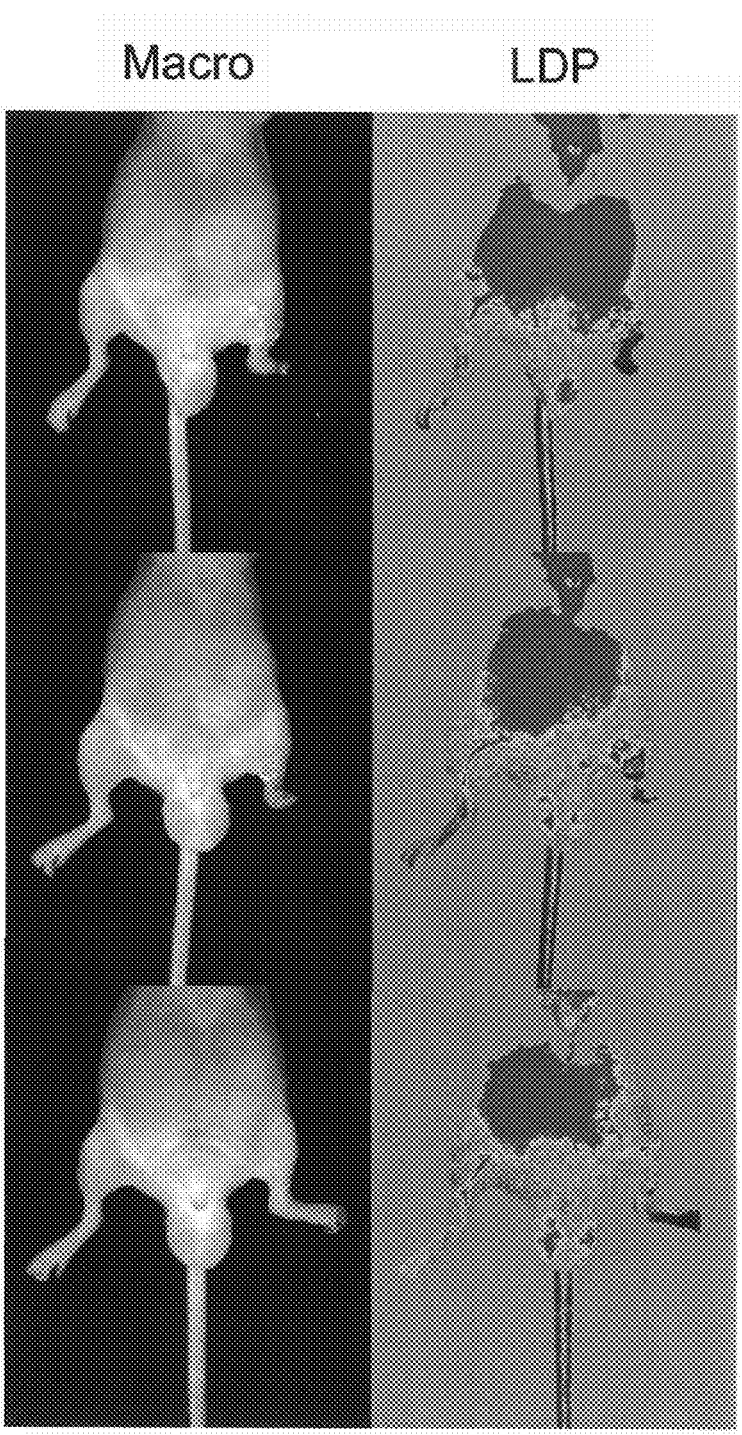
FIG. 1 shows subcutaneous blood perfusion by the laser Doppler method of ischemic limbs treated with adeno-associated virus-mediated PGIS gene (AAV-PGIS group), saline (control group), adeno-associated virus-mediated EGFP gene (AAV-EGFP (enhanced green fluorescence protein) group) and the corresponding macroscopic images.

Particularly, this drug composition of angiogenesis therapy is characteristic of the recombinant adeno-associated virus (AVV) inserted with the gene for production of a factor inducing angiogenesis.

Noteworthy, the present investigation is concerned with the drug composition of angiogenesis used for the treatment or prevention of peripheral arterial disease, which contains the adeno-associated virus (AVV) inserted with human gene for PGIS producing prostaglandin $I_2$ which at least induces the activities of anti-platelet aggregation, vasodilation, and/or angiogenesis or the recombinant adeno-associated virus (AVV) inserted with the gene for the angiogenesis factor.

Here, the use of types 1 or 2 is efficient as the adeno-associated virus (AVV).

The drug composition for angiogenesis therapy in the present invention includes a pharmaceutically permissible carrier such as the recombinant adeno-associated virus (AVV) inserted with the gene for human PGIS or human PGIS and the angiogenesis factor.

The gene coding for the angiogenesis factor used in the drug composition for angiogenesis therapy of the present invention is possibly the entire or a part of the gene coding for a protein or a peptide, which can newly induces vasculogenesis.

Especially, as the gene for angiogenesis factor, vascular endothelial growth factor (VEGF) is acceptable.

The present invention, as described previously, presents a drug composition for angiogenesis therapy useful in treatment or prevention of peripheral arterial disease, which includes human gene for PGIS (hPGIS) producing prostaglandin $I_2$ which induces the activities of vasodilation, and/or anti-platelet aggregation, and the recombinant adeno-associated virus (AVV) inserted with the gene for the angiogenesis factor In use of the present angiogenesis therapy, the "gene for angiogenesis" inserted in adeno-associated virus (AAV) is, similarly to the human PGIS gene, the gene coding for the entire or a part of a protein or a peptide, which newly induces vasculogenesis and shows either activity of inhibition of platelet aggregation, vasodilation, angiogenesis. Namely listed are gene for endothelial growth factor (VEGF), VEGF-2, acidic FGF (aFGF), basic FGF (bFGF), TGF-α, TGF-β, platelet-derived endothelial growth factor (PD-ECGF), platelet-derived growth factor, tumor necrosis factor-α (TNF-α), insulin-like growth factor, angiopoieti-1 etc. Additionally candidates are the gene for HIF-1 and ets family translation factors including ets-1 which regulate the gene expression of VEGF. The genetic sequences of their gene mentioned above are registered in public data bases and are easily cloned by a man of skill in related fields.

Below is an example of gene of VEGF. "VEGF gene" in the present invention indicates the gene coding for VEGF protein and, in some case, simply designates the expression vector (plasmid) encoding the VEGF gene. As concrete illustration a cDNA for VEGF is inserted into the virus vector mentioned after. Regarding human VEGF four subtypes (VEGF121, VEGF165, VEGF189, VEGF206) formed by alternative splicing in transcription of the human gene have been reported (Science, 219, 983, (1983); J. Clin. Invest., 84, 1470 (1989); Biochem. Biophys. Res. Commun., 161, 851 (1989)). Although it is possible in the present invention, that an either subtype of VEGF gene is used for constructing the expression vector, the gene for VEGF165 with the biologically strongest activity is preferable. In addition even the VEGF gene subjected to modifications are classified as the VEGF gene as far as they express the active protein with an angiogenesis activity.

The gene for VGF165 is easily cloned or modified by a man of skill in related fields according to information on the sequence registered in the literature (i.e. Science, 246, 1306 (1989)) or data bases.

The activity expressed by VEGF or its modified gene can be examined in vitro by their growth effect on vascular endothelial cells as described in WO97/07824.

Previously described gene for angiogenesis factors can be used singly or in combination with multiple gene.

Here, $PGI_2$ produced by hPGIS shows the activities of vasodilation, accentuation of vasopermeability and anti-platelet aggregation and a combination of gene for PGIS and an angiogenesis factor brings a more remarkable combination effect.

On the other hand, in the present invention, as "a material with activity of vasodilation" is used $PGI_2$ or preferably its analogs. Additionally, as a "material with activity of anti-platelet aggregation" is also used $PGI_2$ or preferably its analogs.

In the present invention, "the material having activities of vasodilation and/or anti-platelet aggregation" is defined as the compound which produces $PGI_2$ showing activities of vasodilation and/or anti-platelet aggregation, or enhances the production of $PGI_2$. Properly it indicates the compound which enhances synthesis, production of induction of prostaglandin ($I_2$?). Although the suitable compound can be any material including gene, proteins, low molecular weight chemicals etc., the gene for PGIS is utilized as the compound induces the enzyme synthesizing $PGI_2$. The nucleotide sequence of the gene for PGIS are registered in public data bases and its gene is easily cloned by a man of skill in related fields.

Below is an example of gene of human PGIS gene (hPGIS). In the present investigation "PGIS gene" indicates the gene coding for PGIS. Incidentally in some case PGIS gene constructed into an expression plasmid is also described as "PGIS gene". Actually shown as an example is the clone obtained by inserting the PGIS cDNA recorded in B.B.R.C., Vol. 200, No. 3, p 1728-1734 (1994) and WO95/30013 into a proper expression vector. Furthermore, as well as in case of previously described VEGF, the expression constructs with modified PGIS gene are included in the PGIS gene as far as they are the gene coding for protein with the function of PGIS in the present investigation.

The present PGIS gene, as well as the VEGF gene, is also easily cloned on the basis of the sequence information described in the previously described reference and registered in public data bases by a man of skill in related fields and its modification of the clone is easily carried out. The expected activity of the protein coded by the present gene can be examined by assaying products, for example, using an enzyme immunoassay using 6-keto Prostaglandin F1α enzyme immunoassay kit (Cayman, Co., catalog #515211), or thin-layer chromatography detecting the products of prostacyclin synthase.

$PGI_2$ as the compound with activities of vasodilation and/or anti-platelet aggregation or $PGI_2$-inducing materials can be singly used or in combination of multiple compounds.

In relation to the present invention, the administration method, conditions and doses of drug composition of angiogenesis therapy are described below.

1) When used are $PGI_2$ with activities of vasodilation and/or anti-platelet aggregation, and PGIS gene induces the production of PGI$_2$, the gene coding for angiogenesis in use of gene for an angiogenesis factor described above, and the gene coding for angiogenesis in use of combination of gene for PGIS and an angiogenesis factor(s), namely in combination of two or more gene, i.e. the gene for PGIS and VEGF, they need to be in the form of drug for gene therapy.

When the present drug for angiogenesis is administered to a patient, an administration form with the virus vector is given as an example. Experimental manual books particularly describe the methods for preparation and administration of the drug (Separate Volume Jikken-igaku, Fundamental Technique for Gene Therapy (in Japanese), Yodosha Co, 1997; Separate Volume Jikken-igaku, Experimental Methods for Gene Transfer and Expression Analyses (in Japanese), Yodosha Co, 1997; Handbook for R&D of Gene Therapy (in Japanese), ed. The Japan Society of Gene Therapy, NTS Co., 1999). Below the methods for preparation and administration of the drug are explained in detail.

By the way, in the present invention, the objective gene is inserted into the adeno-associated virus (AVV), and can be transferred into the target cells by infection of the recombinant virus (AVV) constructed by insertion of the gene into the adeno-associated virus (AVV) as a vector. Here, types 1, 2, 5, 8 of adeno-associated virus (AVV) are suitable, but types 1 or 2 are preferred.

In the present invention the vector is used for the purpose of transfer of the gene into the target region of the lesion. This selection of adeno-associated virus (AVV) as a vector is due to the efficient transfer of gene into non-dividing cells such as muscle, nerve and liver cells etc. and to the possible long-term expression maintained in these target cells.

Furthermore, the gene therapy drug in the present invention consisting of drug composition of angiogenesis is preferred to be type 1 or 2 of adeno-associated virus (AVV) with an efficient transfer activity of the gene into non-dividing cells such as muscle, nerve and liver cells etc.

Then as the transfer method of the gene-therapeutic drug to the patient, there are two methods: the in vivo method where the gene-therapeutic drug is directly delivered into the body; the ex vivo method where it is ex vivo transfected into a specified cells isolated from the human body and returned to the body (Nikkei Science (in Japanese), April issue, 1994, pp. 20-45; Gekkanyakuji (in Japanese), 36(1), 23-48, 1994; Separate Volume Jikken-igaku, 12(15), 1994; Handbook for R&D of Gene Therapy (in Japanese), ed. The Japan Society of Gene Therapy, NTS Co., 1999). The in vivo method is preferred in the present invention. When the drug for gene therapy is given to the patient, it is delivered in the pathway dependent on the disease as the therapeutic target and the target organ etc. For example the drug for gene therapy is injected into veins, arteries, hypodermic or intracutaneous tissues, and muscles, or directly given to the tissues with the lesion.

As the dose form, various types of dose forms, such as a liquid dose, suitable to their above mentioned administration form can be adoptable. For example, the injection as the dose form containing the active ingredient of a gene can be prepared by common methods. The injection is possibly prepared as follows: the ingredient, for example, is dissolved in a suitable solvent (a buffer such as PBS, saline, sterilized water etc) if necessary, subjected to mechanical sterilization by filtration, and filled in sterilized vessels. A commonly used carrier can be added to the injection. And in use of a liposome such as the HVJ-liposome, the injection can be a suspension, a frozen form or a frozen drug after centrifugal concentration.

And in order to an easy distribution of the gene around the site of the lesion the drug can be embedded around the lesion or slowly and continuously delivered with an osmotic pump.

Incidentally the content of the active pharmaceutical ingredient (API) of the gene can be adjusted according to the disease as the treatment aim, age of patient, body weight etc., is generally in a range of 0.001-100 mg, preferably 0.01-10 mg, which is suitably given to a patient once per days or months.

2) When used are PGI$_2$ with activities of vasodilation and/or anti-platelet aggregation, and PGIS gene induces the production of PGI$_2$, the gene coding for angiogenesis in use of gene for an angiogenesis factor described above, and the gene coding for angiogenesis in use of combination of gene for angiogenesis, and a low-molecular eight chemical, protein, peptide etc., they need to be in the form of drug for gene therapy. On the hand, low-molecular weight chemicals etc. in form of the general drug compositions are administered orally or parenterally. As a typical combination is considerably a combined use of VEGF gene and a PGI$_2$ analog.

The above described drug compositions of low-molecular eight chemicals, proteins etc. as active ingredients are explained below.

When drugs with activities of vasodilation and/or anti-platelet aggregation (anti-platelet drug) are commercially available, their administration methods and dose can be determined according to their protocols. Generally, the dose form and administration method are as follows.

Namely, when the drug is orally administered, it is done in the dose form usually used in the specified field. When the drug is parenterally dispensed, it is administered as the dose form of a focal administration drug, an intrarectal administration drug, an injection, a nasogastric drug etc.

As the oral administration drug or focal administration drug, for example, the dose form of capsules, tablets, pills, powder, drop, suppository, liquid formulation etc. is conceived. For example, a sterilized solution, suspension, and emulsion etc, such as water, a water-propylene glycol mixed solution, a buffered solution, 0.4% saline etc. are conceived as the injection form. The dose form of cream, ointment, lotion, transdermal absorption agent etc. can be chosen as a focal administration drug.

The above dose forms are prepared to the formulations with pharmaceutically tolerably excipients and additives, by common methods employed in the pharmaceutical field. Pharmaceutically tolerably excipients and additives are carriers, binders, incenses, buffering agents, thickening agents, tinctions, stabilizers, emulsifiers, dispersing agents, suspensions, antiseptics, pH-adjusting agents, tonicity-adjusting agents infiltrate agents etc. In addition, pharmaceutically tolerably carriers for example, are magnesium carbonate, lactose, pectin, starch, methylcellulose etc.

When the previously described drug composition is given to the patient, it can be delivered in the pathway dependent on the disease as the therapeutic target and the target organ etc. For example it may be injected into veins, arteries, hypodermic or intracutaneous tissues, and muscles, or directly given to the tissues with the lesion. Additionally the drug composition is also possible to be administered orally or in its suppository form. Incidentally dose and administration frequency of the drug composition is depends on the symptom, age, body weight of a patient, and the administration form. Generally the dose per an adult is in a range of 0.001-100 mg a day, preferably 0.01-10 mg, which is suitably given to a patient once or multiple times divided.

The above mentioned drug compositions with a low-molecular weight chemical or protein as an active ingredient can be administered together with the gene-therapy drug containing the gene for angiogenesis, or separately at regular intervals.

The drug composition of angiogenesis therapy in the present investigation is described above. The present drug composition is useful if treatment or prevention of the peripheral arterial disease, which needs the angiogenesis therapy.

Below the present invention is concretely explained with a practice example, but the present invention is not restricted by this practice example.

Construction of Plasmids and AAV Vectors

The expression vector for human PGIS was constructed as described previously. In brief, the blunted HindIII/BamHI fragment of the full-length human PGIS cDNA was ligated into the blunted XhoI site of the pUC-CAGGS expression plasmid. To verify that the pUC/PGIS construct encoded a biologically active PGIS protein, pUC/PGIS was transfected into NIH3T3 cells, and conversion of [$^{14}$C]-PGH$_2$ to 6-keto-[$^{14}$C]-PGF1α was measured. pUC-CAGGS vector lacking the insert served as the control vector. Human PGIS genes were then inserted into AAV-CAG plasmids, and AAV-hPGIS vectors were constructed. AAV-EGFP (enhanced green fluorescent protein) vector for control experiments was also prepared as described previously.

Murine Model of Hind Limb Ischemia

Eight-week-old male BALB/c nude mice (Japan CLEA) were anesthetized with diethyl ether, and the skin was incised over the femoral artery in the mid-portion of the left hind limb. The femoral artery was then gently isolated, and the proximal portion of the artery was ligated with 7-0 silk ligatures. All experimental procedures and protocols were reviewed and approved by the Animal Care and Use Committee of the Keio University School of Medicine, and they conformed to the NIH Guide for the Care and Use of Laboratory Animals.

Experimental Protocols

Mice were divided into 3 groups (control, AAV-EGFP and AAV-hPGIS). The AAV-hPGIS group was administered AAV type1-hPGIS ($1.0 \times 10^{11}$) into left thigh muscle. The control group was administered the vehicle (0.9% saline) into the left thigh muscle. As negative control, the AAV-EGFP group was administered AAV type1-EGFP ($1.0 \times 10^{11}$) into same site. After 1 week of gene transfer, the left femoral artery of the mice was ligated to produce hind limb ischemia model. After 2 week of ligation, the incidence of limb necrosis was evaluated and blood perfusion rate of the mice was measured using Laser Doppler perfusion imaging (LDPI) system. The left thigh muscles were excised and utilitied for further analysis.

To examine the continuity of the expression of human PGIS mRNA, each 4 to 5 mice in the groups of hPGIS, control, and AAV-EGFP were administered AAV type1-hPGIS ($1.0 \times 10^{11}$, v.g./body), into left thigh muscle of C57/BALB6 mice (8 week-old)

Laser Doppler Blood Perfusion Analysis

The three groups (AAV-hPGIS, CONTROL and AAV-EGFP) of mice are subjected to ischemia in left hind limbs, and the blood perfusion rate in the ischemic left (L) and normal right (R) hind limb was measured with a Laser Doppler perfusion imaging (LDPI) system (Moor LDI, Moor Instruments, USA). The measurement was carried out by taking LDPI of perfusion state of ischemic hind limbs in each group. The results are shown in FIG. 1.

In FIG. 1 optical (Macro) and the corresponding Laser Doppler (LDP) perfusion images obtained by measurement with LDPI system.

In FIG. 1 the images obtained by LDPI method are represented in color. The index for color images representing perfusion state shown below. The index from left to right changes from dark blue to red. Low or nil blood perfusion was displayed as dark blue, and the highest perfusion intervals were displayed as red up to white (maximum).

Figure 2:
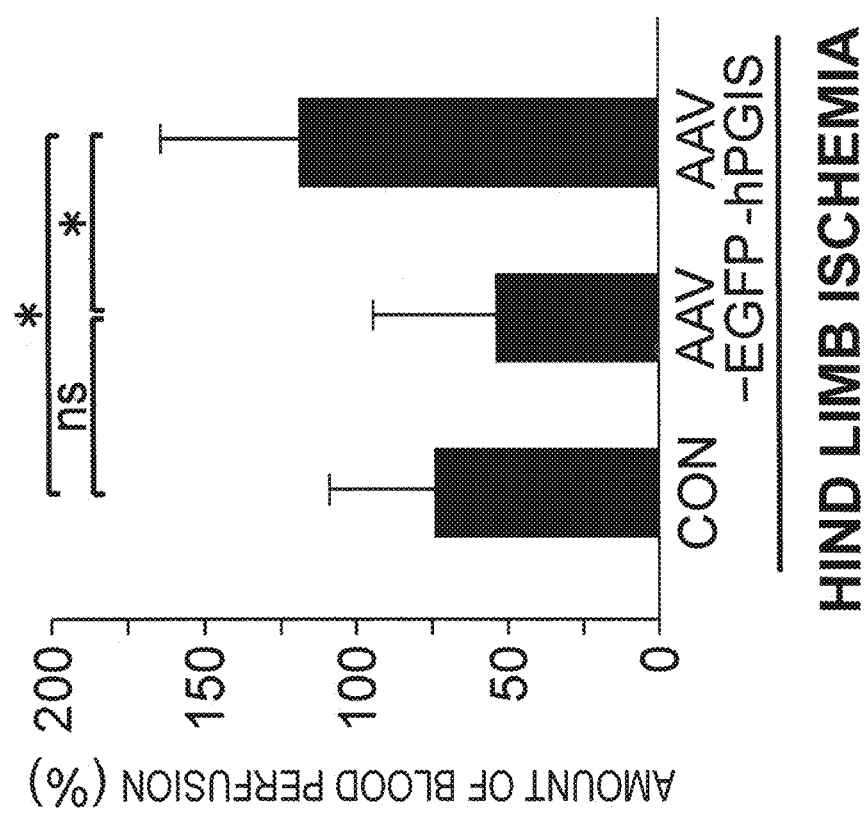
FIG. 2 shows qualitative analyses of perfusion rates of ischemic left limbs treated with adeno-associated virus-mediated PGIS gene (AAV-PGIS), saline (control), adeno-associated virus-mediated EGFP gene (AAV-EGFP) in comparison with the respective control non-ischemic right limbs (n=12)

FIG. 2 shows quantitative analysis of the blood perfusion rate of the ischemic limb in groups of AAV-PGIS, Control and AAV-EGFP, compared with the non-ischemic control limb (n=12). Representative Laser Doppler perfusion images in each group. (B)

In FIG. 2 data are mean±SD. *P<0.05; ns, not significant.

Quantitative RT-PCR

Figure 4:
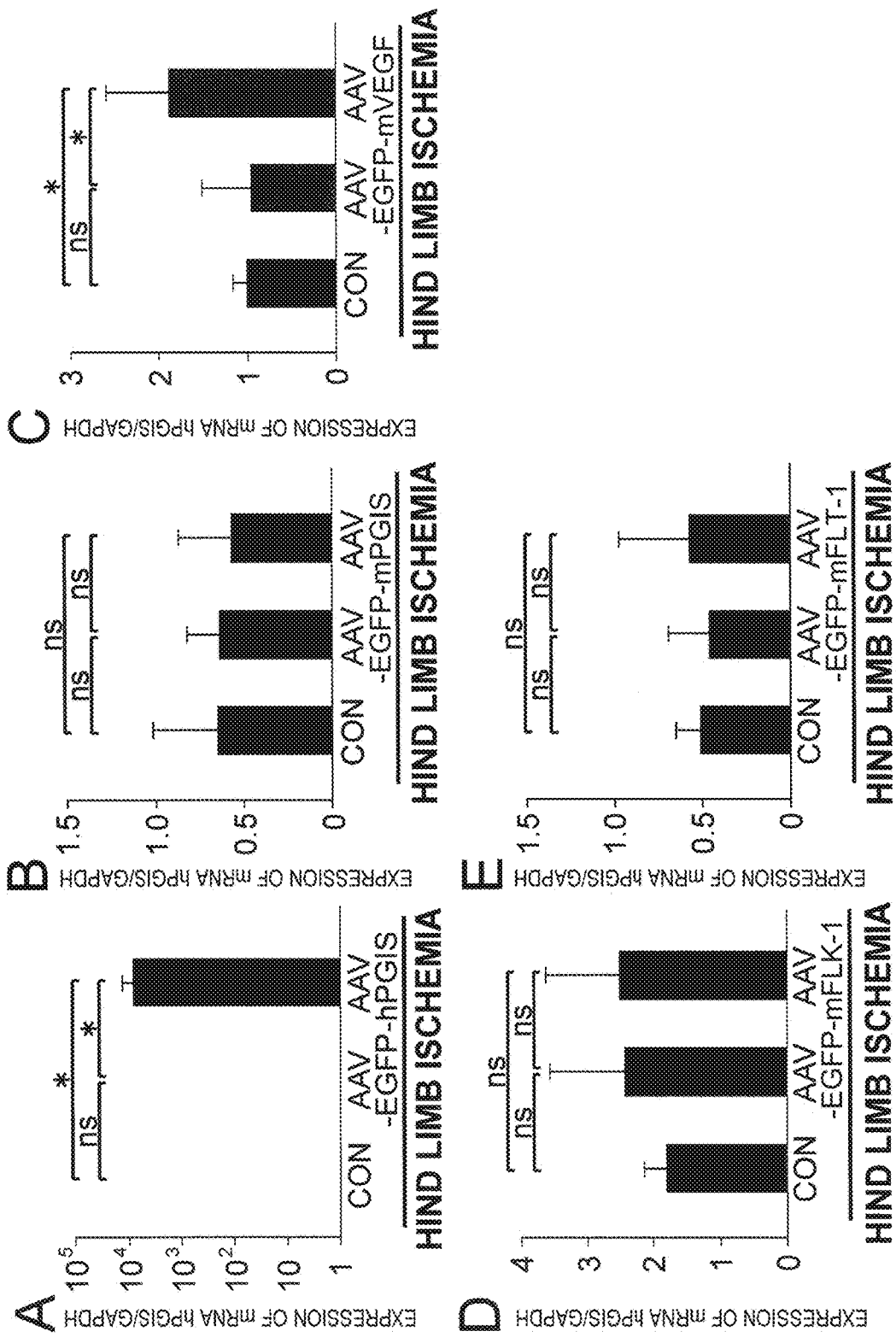
FIG. 4 shows quantitative RT-PCR analysis of the expression of human PGIS, mouse PGIS, mouse VEGF, and a mouse receptor for VEGF, FLK-1 relative to mouse glyceraldehydes-3-phosphate dehydrogenase (GAPDH) mouse in mouse left thigh muscles received an injection of AAV-PGIS, control (saline) or AAV-EGFP. Expression of hPGIS (A), mGAPDH (B), mVEGF (C), and mFLK-1(D) in left limb skeletal muscles were examined by quantitative RT-PCR (n=5).

RNA extraction and quantitative RT-PCR were performed as described previously. Quantitative RT-PCR was performed with TaqMan probes (Applied Biosystems): human PGIS (Hs00168766_m1), mouse PGIS (Mm00447271_m1), mouse VEGF (Mm01281449_m1), FLK-1 (Mm01222419_m1), FLT-1 (Mm00438971_m1), and Rodent GAPDH. The mRNA levels were normalized by comparison to GAPDH mRNA. In FIG. 4 data are mean±SD. *P<0.05; ns, not significant.

Western Blot Analysis

Figure 5:
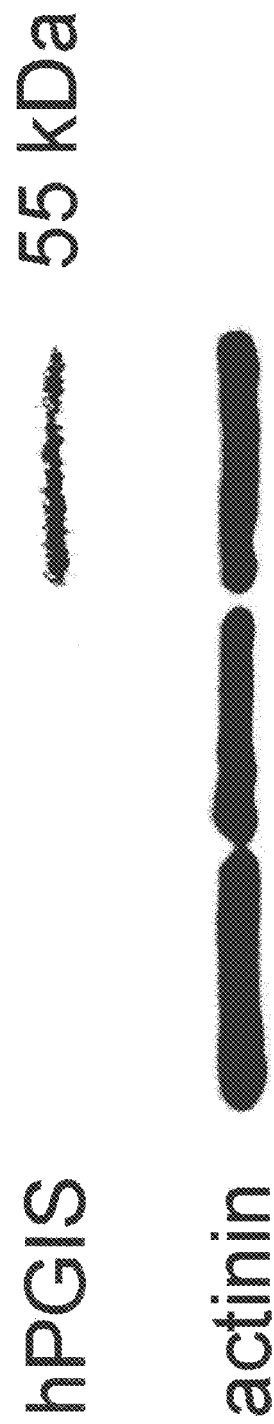
FIG. 5 shows the western blot analysis of the expression of human PGIS (hPGIS) in ischemic muscles received an injection of control (saline), AAV-EGFP or AAV-PGIS.

Membrane fractions of skeletal muscle were prepared by homogenization of thigh muscle in ice-cold buffer as described. Immunodetection was performed on membrane extracts with an antibody to human PGIS. The results are shown in FIG. 5.

Histological Analysis

Samples were fixed with 10% formalin, embedded with paraffin, and cut into 4-μm sections. The sections were stained with hematoxylin and eosin. In addition, thigh muscle sections were stained with anti-human PGIS antibody. The results are shown in FIG. 6, which clearly indicates that the remarkable expression of hPGIS mRNA in group of AAV-hPGIS mice with administration of AAV-hPGIS contributed to angiogenesis.

Figure 6:
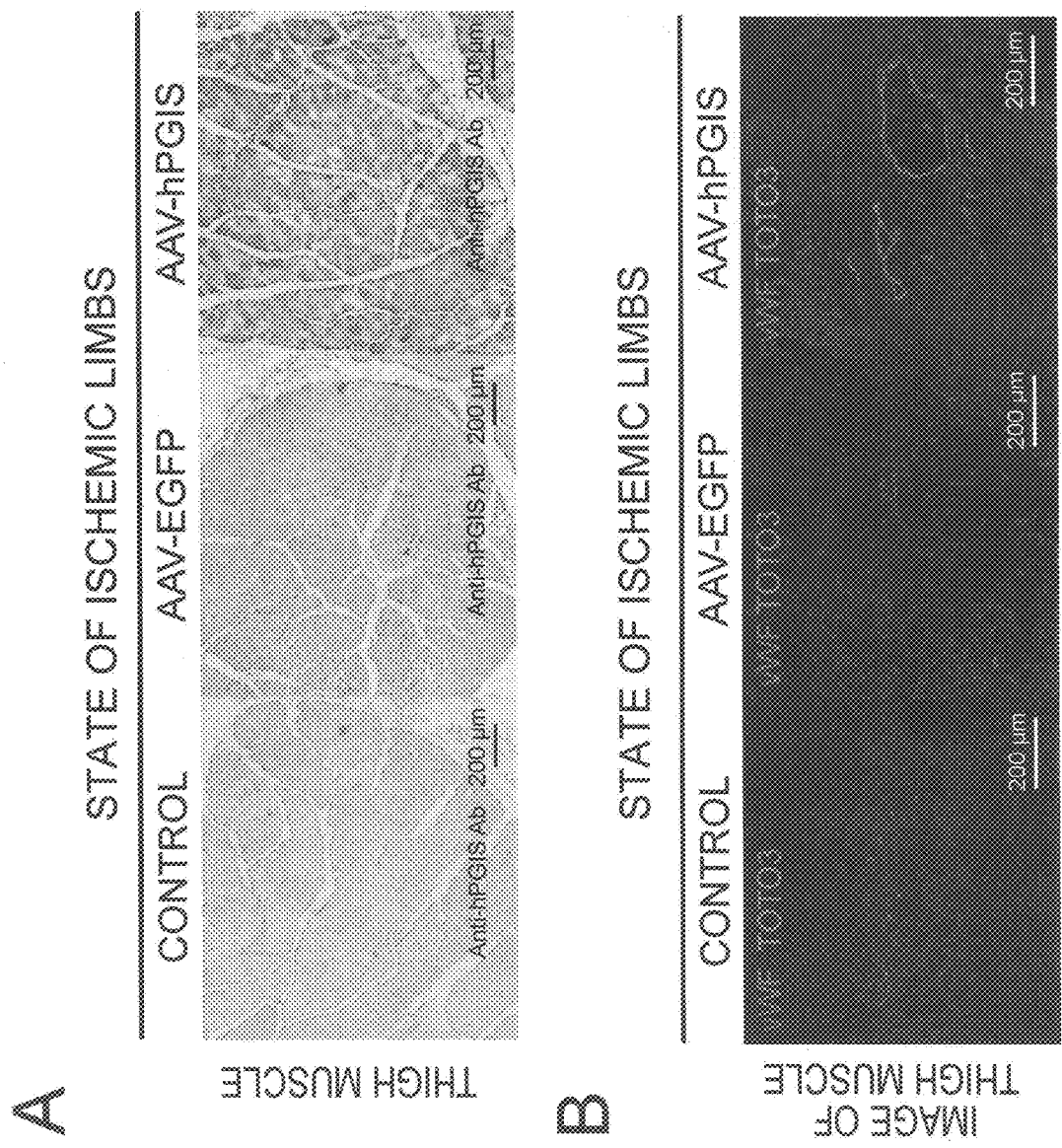
FIG. 6 shows immunostaining images of human PGIS (A) and mouse von Willebrand factor (vWF) (B), and relative capillary vessel area in hind limb muscles received an injection of control (saline), AAV-EGFP or AAV-PGIS. (A) Human PGIS expressed in hind limb muscles received an injection of control (saline), AAV-EGFP or AAV-PGIS was immunostained by anti-human PGIS antibody. (B) Mouse vWF as a neovascularization marker expressed in hind limb muscles in the three groups was immunostained by Anti-vWF antibody. (C) vWF positive area of the images in FIG. 6B was quantitatively analyzed.

In FIG. 6 (A) illustrates microscopic images showing expression of hPGIS in left hind limb muscles in groups of AAV-hPGIS, Control and AAV-EGFP. The each muscle in (A) was stained by immunohistochemical methods. (B) Typical examples of microscopic images of von Willebrand factor (vWF)-stained left hind limb muscles mouse. (C) The results of quantitative analysis of microvessels in left hind limb muscles subjected to immunofluorescence staining of vWF. In FIG. 6C data are mean±SD. *P<0.05; ns, not significant.

Density of Microvessels

Animals were sacrificed under anesthesia, and perfusion fixation was performed with 4% paraformaldehyde. The thigh muscles were excised and embedded with OTC compound. Frozen sections (7 μm) were cut from the tissue specimens. Immunofluorescent staining for endothelial cells was carried out with anti-von Willebrand factor (vWF) antibody (DAKO). Nuclei were stained with TOTO-3 (Molecular Probes). The density of microvessels was calculated from the number of vWF-positive vessels. All confocal microscopy was carried out on a LSM 510 META (Carl Zeiss, Jena, Germany). The capillary density was the ratio between the total area of capillary vessels and the total skeletal muscle area, each measured by Image J software. The data for each mouse were calculated from 30 serial sections.

Statistical Analysis

All data are presented as the mean±SD. Statistical significance was evaluated using the unpaired Student t test.

Comparisons among more than three groups were performed using analysis of variance. P<0.05 was considered significant.

(Experimental Results)

Duration of hPGIS Expression after Administration of AAV Type1-hPGIS Vector

By the present inventors etc. were examined the duration of expression efficiency by AAV type1-hPGIS vector using 8-weeks control mice (C57/BL/6). Mice were administered AAV type1-hPGIS vector into the left thigh muscle. For analysis the left thigh muscle from mice treated with before and after 2, 4, 8, 12 weeks vector administration. The results, as analyzed by quantitative RT-PCR, indicates a strong human PGIS mRNA expression from 2 weeks after gene transfer. The strong expression was maintained even after 12 weeks. The results are shown in Table 1.

TABLE 1

Change in expression of human PGIS after administration of AAV1-human PGIS vector ($1.0 \times 10^{11}$ (v.g./body)) into left thigh muscle

| Term of administration | Number of treated mouse | Amount of expressed human PGIS mRNA*[1] |
|---|---|---|
| Before administration | 8 | 0.003 ± 0.005*[2] |
| 2 weeks after administration of AAV-human PGIS | 4 | 1220 ± 4880 |
| 4 weeks after administration of AAV-human PGIS | 5 | 6310 ± 9470 |
| 8 weeks after administration of AAV-human PGIS | 5 | 4648 ± 2640 |
| 2 weeks after administration of AAV-human PGIS | 5 | 3370 ± 1980 |

*[1]Relative amount of hPGIS mRNA to mouse GAPDH mRNA.
*[2]Mean value ± SD.
*[3]mice were administered AAV1-human PGIS vector ($1.0 \times 10^{11}$ (v.g./body))

Improvement of Hind Limb Ischemia

Figure 3:
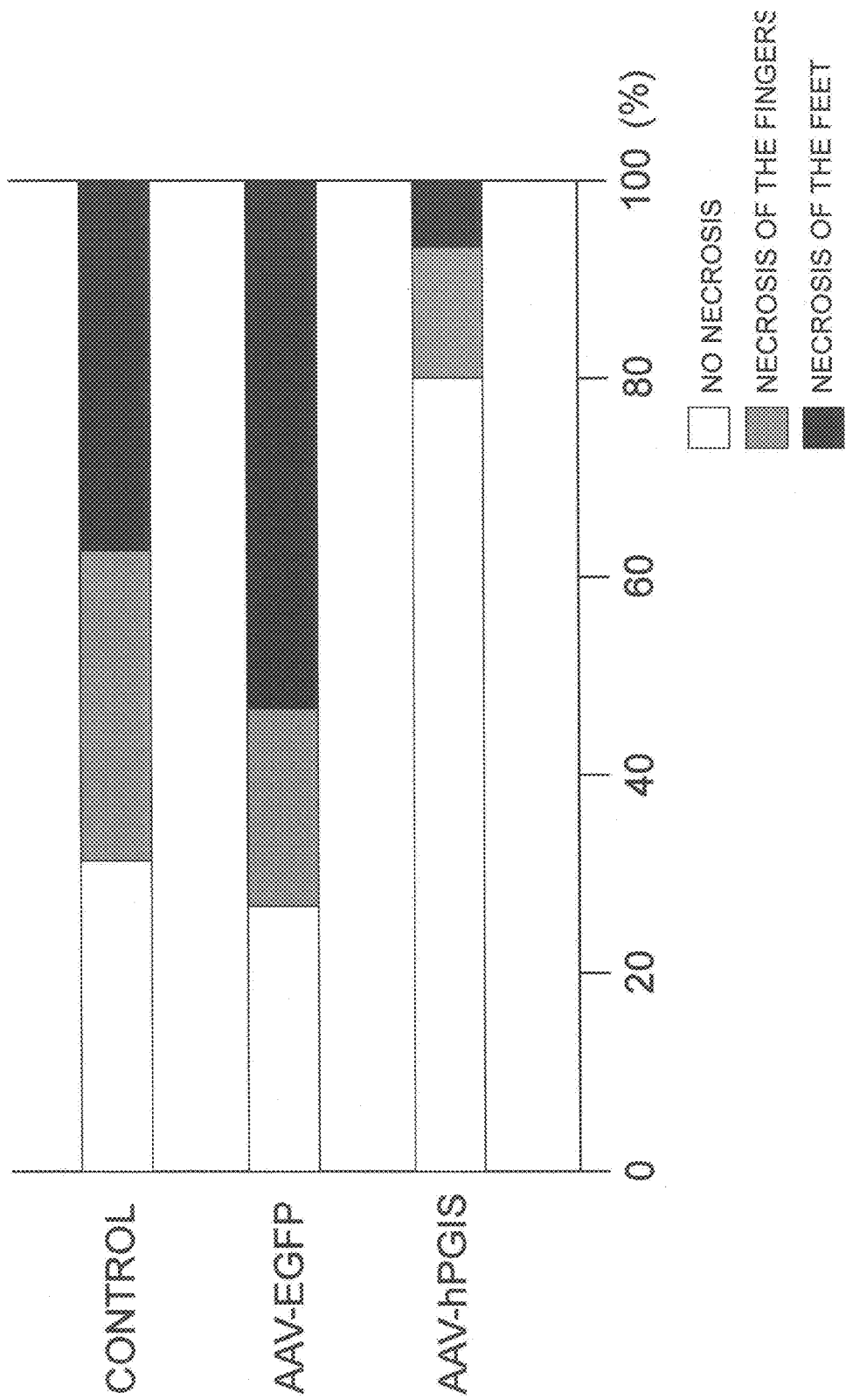
FIG. 3 indicates the improvement in limb necrosis rate of AAV-PGIS group mice in comparison with those of control and AAV-EGFP group mice.

To treat limb ischemia model mice, the present inventor et al administered AAV type1-hPGIS into left thigh muscle and examined the degree of improvement in the ischemia two weeks after the limb-ischemia operation. In examination the seriousness of limb ischemia was divided into three groups. As shown in FIG. 3, foot or finger necrosis was observed in 63% and 69% mice in groups of Control and AAV-EGFP treated with AAV type1-EGFP, respectively. But the rate of necrosis in AAV-hPGIS group mice received an administration of AAV type1-hPGIS, was significantly lowered to 19% and improved. Furthermore, frequency of tertiary foot necrosis in AAV-hPGIS was lowest in the three groups described above. These results indicate the administration of AAV type1-hPGIS in skeletal muscles is effective in limb ischemia.

Laser Doppler Blood Perfusion Analysis

Using laser Doppler blood perfusion (LDP) the blood flow in limb muscle tissues of AAV-hPGIS, Control, and AAV-EGFP group mice was analyzed percutaneously. In the LDP images shown in FIG. 1, the blood perfusion of left thigh muscle tissues in the lesion side of mice was lowered in Control and AAV-EGFP groups compared with AAV-hPGIS group. Additionally quantitative analysis (blood perfusion rate) by LDP method indicates 73, 54 or 118% of perfusion rates in the left lesion side of mice as referred to those in respective right healthy sides in the three groups of Control, AAV-EGFP and AAV-hPGIS (see FIG. 2). It is likely from the remark of LDP images that the administration of AAV-hPGIS improves the blood perfusion.

Analysis of mRNA in Ischemic Muscles

Expression of mRNA in ischemic limb tissues was analyzed using quantitative RT-PCR.

Compared with Control and AAV-EGFP groups, a remarkably significant expression of human PGIS gene was observed in AAV-hPGIS group (see FIG. 4A) and the expression of intrinsic mouse PGIS gene was not significantly different among the three group mice. Furthermore, expression of murine mRNA for VEGF, FLK-1 and FLT-1 was analyzed to study neovascularization in the ischemic limb tissues. Consequently, it was significant that expression of VEGF mRNA in AAV-PGIS group was twice compared with that in the other two groups (See FIG. 4C). Although expression of mRNA for FLK-1 and FLT-1 in AAV-PGIS group has an increasing tendency compared that in the other two groups, the difference was not statistically significant among them (see FIGS. 4D and 4E). Hereinbefore, strong expression of hPGIS was confirmed in skeletal muscles. Additionally, expression of VEGF mRNA increased in AAV-PGIS group.

Western Blot Analysis of Ischemic Muscles

Furthermore, gene expression at protein level was examined using western blot analysis. Western blots confirmed hPGIS protein in AAV-hPGIS administration group (see FIG. 5).

Expression of hPGIS in Skeletal Muscles

Moreover, histological examination of the skeletal muscle of the region administered AAV-PGIS was carried out. Immunostaining with anti-human PGIS antibody confirmed expression of hPGIS gene/protein in muscle cells in AAV-hPGIS administration group (see FIG. 6), and none of immunological changes such as infiltration of inflammatory cells was observed among the three groups administered AAV-PGIS, Control and AAV-EPDGF.

Angiogenesis in Skeletal Muscles

Additionally to examine improvement at the level of ischemic muscle cells, skeletal muscles were subjected to immunostaining with anti-vWF antibody. In confocal microscopy the increase in vEF-positive vessels was observed in AAV-hPGIS group compared with Control and AAV-EGFP groups, suggesting an increase in capillary density (see FIGS. 6A and 6B). Thus, the density of vVW-positive microvessels was quantitatively analyzed using Image J software.

The capillary density was expressed as the ratio between the total area of capillary vessels and the total skeletal muscle area. It was statistically significant that the density of vVW-positive microvessels in AAV-hPGIS group was 6.5 folds higher than that in Control and AAV-EGFP groups (see FIG. 6C). Elastica van Gieson (EGV) stain of skeletal muscles was also carried out, but any significant change was not observed among the above three groups.

As described above, neovascularization at the capillary level occurred in the ischemic skeletal muscles administered AAV-PGIS, suggesting reduction of ischemic injury of skeletal muscles.

It is shown from the facts described above that improvement of hind limb ischemia is obtained by transfer of human PGIS gene in ischemic skeletal muscles using AAV type 1 vector. Although many serotypes are known as AVV, AAV type 1 is known to have an ability of the strongest and long-term expression in skeletal muscles. It is reported by the present inventor et al that AAV type 1-human PGIS (AAV-hPGIS) shows a long-term strong gene transfer efficiency in the in vitro and in vivo control experiments.

Additionally gene expression of AAV type 1 is limited in the local site of administration, and it is not found in remote organs. This characteristic of the expression can reduce the side effect of the gene therapy in remote organs, and is useful in the treatment of patients suffering from serious limb ischemia, which are complicated with arteriosclerosis-induced diseases in other organs.

As it is clear from previously described experimental results, the rate of necrosis in AAV-hPGIS group mice received an administration of AAV type1-hPGIS, was significantly lowered and frequency of tertiary foot necrosis was lowest in AAV-hPGIS. Furthermore, in quantitative analysis by LDP the perfusion rate in AAV-hPGIS group caused a statistically significant increase compared with those in the two groups without administration of AAV-hPGIS. LDP image suggests that the development of collateral vessels contribute to the improvement of blood perfusion in ischemic limbs, because disruption of blood perfusion in femoral arteries by ligation, namely the blockage of femoral arteries was confirmed in all groups.

Subsequently, gene expression was examined with skeletal muscles, the administration site of AAV-hPGIS. The expression of PGIS gene was analyzed by quantitative RT-PCR. A remarkable gene expression of external human PGIS was observed with skeletal muscles in AAV-hPGIS group, and was ten thousand-folds compared with those of the control groups. An enhanced two-fold gene expression of intrinsic VEGF was also observed with skeletal muscles in AAV-hPGIS group, suggesting induction of VEGF by expression of external human PGIS. Using immunostaining of hPGIS a remarkable expression of human PGIS protein was observed in skeletal cells mediated AAV-hPGIS. In addition, any inflammatory changes and tumor formation of muscles was not found by the AAV viral administration. The findings prove the safety of AAV-PGIS, and coincide with the fact that AAV has the lowest immunogenicity among virus vectors.

Furthermore, by the present inventors skeletal muscles was subjected to immunostaining with anti-vWF antibody in order to examine whether neovascularization occurs or not. In AAV-PGIS group neovascularization was confirmed at the capillary level. Incidentally EVG-staining for elastic fibers in skeletal muscles was carried out and significant changes were not observed in all treated groups, suggesting that the neovascularization at capillary level occurs in skeletal muscles administered AAV-hPGIS.

It is demonstrated from results mentioned above that transfer of AAV-hPGIS into skeletal muscles improves limb ischemia by a remarkable expression of human PGIS in skeletal muscle cells, leading to production in the muscle cells and secretion of $PGI_2$ meditated by the expression, which induces activities of vessel protection, induction of neovascularization etc. And it is noteworthy that the effects mentioned above were achieved by single administration. Previous clinical and basic research reports reveal that the strong continuous gene expression could not be maintained due to plasmids, non-viral vectors etc. without a property of long-term expression. Thus, with use of these vectors the multiple-time administration is necessary to keep the gene expression. The highly safe virus vectors such as the AAV vector achieving a long-term and strong expression can be ideal for clinical applications

What is claimed is:

1. A method for inducing production of vascular endothelial growth factor (VEGF), the method comprising: administering, to an individual, a composition comprising an adeno-associated virus (AAV) carrying a hPGIS gene coding for human prostacyclin synthase (hPGIS) and a second gene coding for an angiogenesis factor selected from the group consisting of genes coding for vascular endothelial growth factor (VEGF) and VEGF-2, wherein the hPGIS synthesizes prostaglandin $I_2$ ($PGI_2$) and induces production of VEGF in the individual, and wherein the AAV induces the activities of vasodilation, anti-platelet aggregation, and angiogenesis.

2. The method according to claim 1, wherein the AAV is of a type selected from the group consisting of type 1, 2, 5 and 8.

3. The method according to claim 1, wherein the AAV is of a type selected from the group consisting of type 1 and 2.

4. The method according to claim 1, wherein the composition further comprises a pharmaceutically permissible carrier containing the AAV, the carrier being selected from the group consisting of water, a water-propylene glycol mixed solution, a buffered solution, and 0.4% saline.

* * * * *